United States Patent [19]

Zelter

[11] Patent Number: 4,746,567
[45] Date of Patent: May 24, 1988

[54] PAPER PRODUCT FOR STORING FRAGRANCES

[75] Inventor: Jean-Claude E. Zelter, Grasse, France

[73] Assignee: Ylang, Grasse, France

[21] Appl. No.: 944,218

[22] Filed: Dec. 22, 1986

[51] Int. Cl.$^4$ ............................................. B01J 13/02
[52] U.S. Cl. ................................ 428/321.5; 428/905; 503/200; 503/207
[58] Field of Search ................... 428/321.5, 542.8, 905; 503/200, 207

[56] References Cited

U.S. PATENT DOCUMENTS

| | | | |
|---|---|---|---|
| 3,516,846 | 6/1970 | Matson | 428/321.5 X |
| 3,623,659 | 11/1971 | Maierson et al. | 428/905 X |
| 3,640,629 | 2/1972 | Geiser | 428/167 X |
| 3,825,467 | 7/1974 | Phillips, Jr. | 428/321.5 X |
| 3,849,234 | 11/1974 | Pottkotter | 428/40 X |
| 3,996,060 | 12/1976 | Johnson | 428/321.5 X |
| 4,145,001 | 3/1979 | Weyenberg et al. | 428/905 X |
| 4,243,224 | 1/1981 | Spector | 428/905 X |
| 4,277,024 | 7/1981 | Spector | 239/36 |
| 4,283,011 | 8/1981 | Spector | 428/79 X |
| 4,579,770 | 4/1986 | Matsushita et al. | 428/321.5 X |
| 4,596,996 | 6/1986 | Sandberg et al. | 503/207 |
| 4,606,956 | 8/1986 | Charbonneau et al. | 428/905 X |
| 4,661,388 | 4/1987 | Charbonneau et al. | 428/905 X |

Primary Examiner—Henry F. Epstein
Attorney, Agent, or Firm—Hughes, Cassidy & Multer

[57] ABSTRACT

A paper product for storing fragrances comprises a paper support in which there is embedded a quantity of microcapsules in some of which there is encapsulated a fragrant essence while others are without fragrance, e.g., filled with a neutral fluid. The microcapsules are incorporated in the paper during its preparation from paste. Those neutral microcapsules preserve the integrity of the fragrance-containing microcapsules during handling of the product. The captive fragrance may be released after an indefinite storage period by deliberate crushing or otherwise rupturing of the microcapsules. The product may be a scented card, publicity insert, unwoven paper tissue or the like, and the main application of the invention lies in the perfume industry.

6 Claims, 1 Drawing Sheet

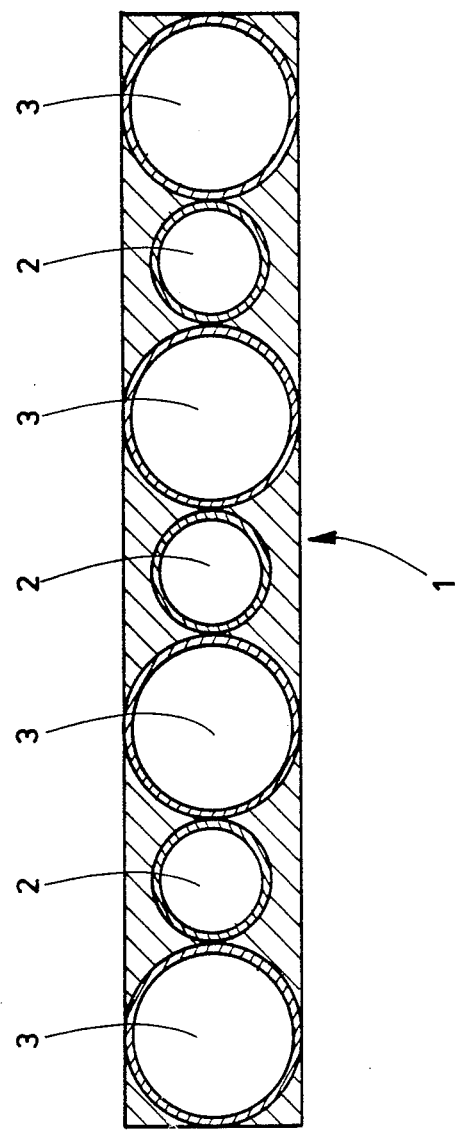

PAPER PRODUCT FOR STORING FRAGRANCES

FIELD OF THE INVENTION

The invention relates to a paper product such as scented card, publicity inserts, unwoven paper tissues and the like in which a fragrance is provided by encapsulation within microcapsules which can be crushed by rubbing to release the fragrance.

BACKGROUND OF THE INVENTION

Paper supports such as publicity inserts are known which are scented by spraying with or dampening in the selected fragrance. At first this type of scented card when placed in a magazine or newspaper will release a strong odour which then fades and completely disappears in such a way that the reader cannot appreciate the olfative qualities of the presented fragrance.

Also known are publicity inserts for magazines and the like comprising a pocket into which a scented card is slipped. The fragrance thus stored by spraying with or dampening in the scent, is a little better protected. However, the manufacture of such an insert is extremely lengthy and costly.

Further known products include publicity cards or inserts in which the fragrance is stored in microcapsules of around a tenth of a millimeter, stuck in the form of a layer on the card support. The layer of microcapsules containing the fragrance is protected by a protective flap. This solution has the advantage of preserving intact the olfative qualities of the fragrance until the publicity insert reaches the reader. The latter lifts the flap and by rubbing or scratching crushes the microcapsules releasing the stored fragrance. This type of publicity insert is however very difficult to manipulate and requires a long manufacturing process consisting of a number of operations. The card support has to be coated with a layer of adhesive, then the layer of microcapsules is added by blowing the capsules onto the layer of adhesive. Finally, the layer of capsules is covered by a protective flap. Despite this protective flap, the capsules are fragile due to the fact that they are superimposed on the card support.

Furthermore, the size of these microcapsules, approximately one tenth of a millimeter, also gives increased fragility.

OBJECTS OF THE INVENTION

An object of the present invention is to provide a paper product, such as a scented card, publicity insert, unwoven paper etc, which has no fragrance before the capsules are crushed, thereby preserving the olfactive qualities of the stored fragrance until the publicity insert reaches its destination.

Another object of the invention is also to provide a paper product allowing several fragrances to be presented in the same periodical.

Yet another object of the present invention is also to provide a paper product which preserves the microcapsules storing the fragrance against any crushing during production of the papers or their distribution.

Finally, a further object of the present invention is to provide a paper product presenting fragrances at an extremely low cost price, while allowing the olfactive qualities of the stored and presented fragrance to be tested in the best conditions.

SUMMARY OF THE INVENTION

An olfactory product is formed by encapsulating a fragrance within microcapsules which are then incorporated in a paper paste from which a paper support is formed.

Thus, the invention relates to a paper support such as a scented card, publicity insert, unwoven paper or the like which receives a small quantity of fragrance stored in microcapsules which can be crushed by rubbing in order to release the fragrance, the paper support being characterised in that the microcapsules storing the fragrance are embedded when the paste is prepared.

In accordance with a preferred characteristic of the invention, the microcapsules storing the fragrance are small hollow balls of gelatine with a diameter of about 5 microns.

The present invention will be better understood through the following exemplary and non-limiting embodiment of a paper support.

DESCRIPTION OF THE DRAWING

A cross section of a paper support containing microcapsules for storing the fragrance and neutral microcapsules serving as shock absorbing elements is shown in the single fIGURE attached.

DESCRIPTION OF A PREFERRED EMBODIMENT

According to the FIGURE, the paper support 1 shows, in section, a scented card, a publicity insert or any other support for presentation, particularly of fragrances. The invention extends to non-woven paper such as disposable handkerchiefs. The paper support 1 contains microcapsules for storing fragrance 2. These microcapsules for storing fragrance are embedded when the paper paste is prepared. The microcapsules for storing the fragrance 2 are small hollow balls of gelatine with a diameter of 5 microns.

Furthermore, the paper support 1 consists of neutral microcapsules 3 filled with a fluid, ie, air or liquid which have no olfative qualities. These neutral microcapsules 3 are also hollow balls of gelatine embedded when the paper paste is prepared. The diameter of microcapsules 3 is considerably greater than the diameter of the microcapsules for storing the fragrance 2.

Microcapsules 3 with a larger diameter serve as shock absorbing elements to protect the microcapsules for storing fragrance against crushing due to the various manipulations of paper 1.

An original feature of the invention is therefore to embed the microcapsules containing the fragrance as well as the larger diameter shock absorbing microcapsules which are to prevent crushing.

Microcapsules 2 preserve all the olfactive qualities of the fragrance until the user destroys the capsules by rubbing or scratching.

The microcapsules for storing the fragrance 2 have a diameter of about 5 microns which is perfect for inclusion in a paper support weighing about 15 g per square meter.

The neutral microcapsules 3 are to protect microcapsules 2 against crushing, especially during manufacture of the paper support 1, where at a certain stage of the process it passes between two cylinders which subject it to intense pressure.

The same happens when the paper support is subjected to the action of printing presses.

The term "paper support" is to be understood in its widest sense, ie, "any material manufactured by means of stationery techniques".

It will be appreciated that whilst the invention has been described with reference to the attached FIGURE, this is merely illustrative of an embodiment of the invention, the scope of the invention being significantly broader as defined in the patent claims hereinafter appearing. Further, it will be realised by those skilled in the art that the invention may be applied to store any odour in a paper support so that the term "fragrance" is intended to encompass all agents capable of stimulating an olfactory sensation. Therefore, whereas the invention finds its main application in the perfume industry, it may be usefully applied for other advertising and marketing purposes.

I claim:

1. A paper product for storing a fragrance comprising a paper support and microcapsules containing a fragrance, the said microcapsules being incorporated in the paper support, said fragrance being releasable upon crushing of the microcapsules by rubbing or like action, said paper product being further characterized in that in addition to said microcapsules containing a fragrance, said paper support incorporates neutral microcapsules without fragrance which are disposed in the paper support in a manner to serve as shock-absorbing means to protect the said microcapsules containing a fragrance from accidental crushing.

2. The paper product of claim 1 wherein the neutral microcapsules are of larger diameter than those containing a fragrance.

3. The paper product of claim 2 wherein the microcapsules used to contain the fragrance are small hollow balls of gelatine with a diameter of about 5 microns.

4. The paper product of claim 1 wherein the microcapsules used to contain the fragrance are small hollow balls of gelatine with a diameter of about 5 microns.

5. The paper product of claim 1 wherein the said neutral microcapsules are hollow balls of gelatine filled with a fluid.

6. The product as recited in claim 1, wherein said microcapsules are incorporated in the paper support during its preparation from a paste by addition of said microcapsules to said paste.

* * * * *